US 11,395,683 B2

(12) United States Patent
Schwiesau et al.

(10) Patent No.: US 11,395,683 B2
(45) Date of Patent: Jul. 26, 2022

(54) SURGICAL CONNECTION DEVICE AND SURGICAL CONNECTION SYSTEM

(71) Applicant: Aesculap AG, Tuttlingen (DE)

(72) Inventors: Jens Schwiesau, Tuttlingen (DE); Sven Krüger, Trossingen (DE)

(73) Assignee: AESCULAP AG, Tuttlingen (DE)

( * ) Notice: Subject to any disclaimer, the term of this patent is extended or adjusted under 35 U.S.C. 154(b) by 0 days.

(21) Appl. No.: 17/209,453

(22) Filed: Mar. 23, 2021

(65) Prior Publication Data
US 2021/0298793 A1 Sep. 30, 2021

(30) Foreign Application Priority Data
Mar. 25, 2020 (DE) .................... 10 2020 108 276.2

(51) Int. Cl.
A61B 17/70 (2006.01)
A61B 17/00 (2006.01)

(52) U.S. Cl.
CPC ............ A61B 17/7049 (2013.01); A61B 2017/00477 (2013.01)

(58) Field of Classification Search
CPC ...................... A61B 17/7049–7052
See application file for complete search history.

(56) References Cited

U.S. PATENT DOCUMENTS

| 5,624,442 | A  | * | 4/1997  | Mellinger  | A61B 17/7037 606/250 |
| 7,175,622 | B2 | * | 2/2007  | Farris     | A61B 17/705 606/250 |
| 8,998,961 | B1 | * | 4/2015  | Ziemek     | A61B 17/86 606/278 |
| 10,321,939 | B2 | * | 6/2019  | Lee        | A61B 17/7049 |
| 2005/0228378 | A1 | * | 10/2005 | Kalfas     | A61B 17/705 606/252 |
| 2007/0173825 | A1 | * | 7/2007  | Sharifi-Mehr | A61B 17/705 606/272 |
| 2007/0270817 | A1 | * | 11/2007 | Rezach     | A61B 17/7049 606/252 |
| 2008/0262553 | A1 | * | 10/2008 | Hawkins    | A61B 17/705 606/278 |
| 2010/0280552 | A1 |   | 11/2010 | Lee        | |
| 2011/0106166 | A1 |   | 5/2011  | Keyer et al. | |
| 2012/0029571 | A1 |   | 2/2012  | Schwab et al. | |
| 2013/0018421 | A1 | * | 1/2013  | George     | A61B 17/56 606/278 |
| 2017/0348026 | A1 | * | 12/2017 | Stein      | A61B 17/7049 |

(Continued)

FOREIGN PATENT DOCUMENTS

WO 2009001978 A1 12/2008

Primary Examiner — Eduardo C Robert
Assistant Examiner — Steven J Cotroneo
(74) Attorney, Agent, or Firm — Christopher A. Rothe; Culhane Meadows, PLLC

(57) ABSTRACT

A surgical connection device for connecting two rod elements in one or more relative orientation includes a main body with receiving openings. The rod elements can be fixed to the main body by fixing elements. At least one receiving opening has an aperture at a receiving opening edge, through which aperture a rod element can be inserted into the receiving opening transversely to the orientation of the receiving opening. A connection system includes a surgical connection device and two or more rod elements.

19 Claims, 5 Drawing Sheets

(56) References Cited

U.S. PATENT DOCUMENTS

2018/0098798 A1    4/2018  Italiaie et al.
2018/0125538 A1*   5/2018  Daniels .............. A61B 17/7056
2019/0388125 A1*  12/2019  Ahn ........................ A61B 17/86
2021/0030448 A1*   2/2021  Yoder ................ A61B 17/7041

* cited by examiner

SURGICAL CONNECTION DEVICE AND SURGICAL CONNECTION SYSTEM

CROSS-REFERENCE TO RELATED APPLICATIONS

This application claims the benefit of German application number 10 2020 108 276.2, filed on Mar. 25, 2020, which is incorporated herein by reference in its entirety and for all purposes.

FIELD

The present disclosure relates to a surgical connection device for connecting a first rod element to a second rod element in a relative orientation, in particular in two or more relative orientations, wherein the connection device comprises a main body with a first connection region for the first rod element and a second connection region for the second rod element, wherein at least three receiving openings are formed in the main body, wherein at least one of the receiving openings is arranged in each connection region and at least one connection region has two or more of the receiving openings with different axes from one another, into which receiving openings the rod element is insertable selectively, and wherein in each connection region there is arranged a fixing element for fixing the respective rod element at the connection region in a fixing direction.

The present disclosure additionally relates to a surgical connection system having a connection device of the above-mentioned type and two or more rod elements, which are fixable selectively to the first connection region and/or to the second connection region.

BACKGROUND

The connection device described at the outset is used in a surgical setting, for example to connect rod elements which are fixed to anchoring elements, in particular bone screws. The rod elements should preferably be able to assume different relative orientations depending on the application. For this reason, the connection device is provided such that the first rod element can be fixed at the first connection region and the second rod element can be fixed at the second connection region in one or more relative orientations with respect to one another. Here, each rod element can, for example, engage at least in sections in a receiving space of the first connection region. It is also known that the rod elements may have different characteristics. In particular, rod elements of different diameter are provided. In practice, it has been found that a large number of different connection devices and rod elements are kept available and are utilized depending on the particular application. This makes storage more complicated. Intraoperative flexibility suffers. Preparation is made more complicated. Storage and/or preparation require larger screen baskets, the stocking of which with equipment is confusing. This may result in high expenditure.

A generic connection device and a generic connection system are described, for example, in U.S. Pat. No. 8,998, 961 B1. Further surgical connection systems are disclosed in US 2012/0029571 A1, US 2008/0125538 A1 and US 2017/0348026 A1

An object underlying the present disclosure is to provide a connection device and a connection system that can be handled more easily.

SUMMARY

In a first aspect, a surgical connection device for connecting a first rod element to a second rod element in a relative orientation, in particular in two or more relative orientations is provided. The connection device comprises a main body with a first connection region for the first rod element and a second connection region for the second rod element. At least three receiving openings are formed in the main body. At least one of the receiving openings is arranged in each connection region and at least one connection region has two or more of the receiving openings with different axes from one another, into which receiving openings the rod element is insertable selectively. In each connection region there is arranged a fixing element for fixing the respective rod element at the connection region in a fixing direction. One of the receiving openings is formed in a first surface portion of the main body, the receiving opening edge of which receiving opening has an aperture, which extends from the first surface portion to an adjacent second surface portion of the main body, the second surface portion being angled with respect to the first surface portion, for inserting the rod element into the receiving opening starting from the second surface portion and through the aperture, in an insertion direction transverse to the axis and transverse to the fixing direction.

In a second aspect, a surgical connection system is provided which comprises at least one connection device in accordance with the first aspect and two or more rod elements, which are fixable selectively at the first connection region and/or at the second connection region.

BRIEF DESCRIPTION OF THE DRAWINGS

The foregoing summary and the following description may be better understood in conjunction with the drawing figures, of which.

DETAILED DESCRIPTION

Figure 1:
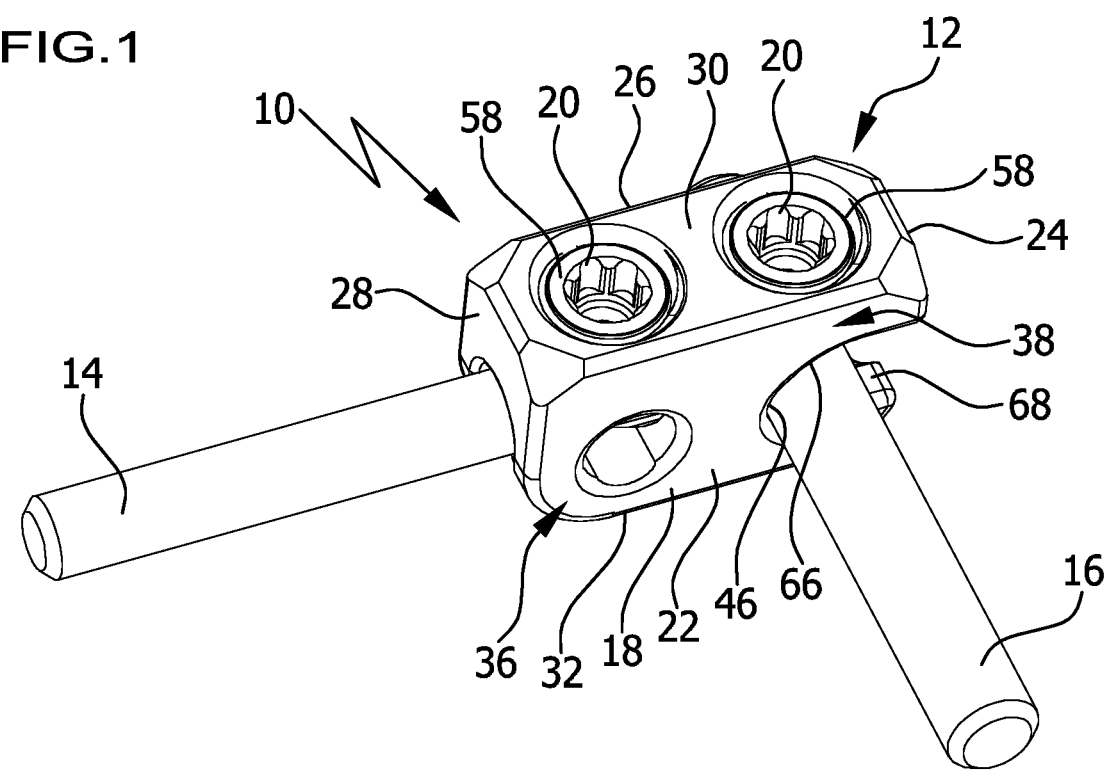
FIG. 1: shows a first perspective view of a connection system in accordance with the disclosure, comprising a connection device in accordance with the disclosure and two rod elements in a first relative orientation.

Although the present disclosure contains specific embodiments, the scope of this disclosure is not intended to be limited to the details shown. Rather, various modifications may be made in the details within the scope and range of equivalents and without departing from the disclosure.

The present disclosure relates to a surgical connection device for connecting a first rod element to a second rod element in a relative orientation, in particular in two or more relative orientations, wherein the connection device comprises a main body with a first connection region for the first rod element and a second connection region for the second rod element, wherein at least three receiving openings are formed in the main body, wherein at least one of the receiving openings is arranged in each connection region and at least one connection region has two or more of the receiving openings with different axes from one another, into which receiving openings the rod element is insertable selectively, and wherein in each connection region there is arranged a fixing element for fixing the respective rod element at the connection region in a fixing direction. One of the receiving openings is formed in a first surface portion of the main body, the receiving opening edge of which receiving opening has an aperture which extends from the first surface portion to an adjacent second surface portion of the main body being angled with respect to the first surface portion, for inserting the rod element into the receiving opening starting from the second surface portion and through the aperture, in an insertion direction transverse to the axis and transverse to the fixing direction.

The connection device in accordance with the disclosure has at least one receiving opening in each connection region, with two or more receiving openings being provided in at least one connection region, so that the rod elements can preferably also be fixed in relative orientations that differ from one another. The term "axis" is to be understood in the present context in particular to the effect that a particular receiving opening defines an orientation (direction, especially away from the main body, and position) of the rod element arranged correctly in the receptacle. In accordance with the disclosure, a receiving opening is provided on a first surface portion, the receiving opening edge of which receiving opening has an aperture. This makes it possible to insert the rod element to be fixed starting from a second surface portion into the receiving opening through the aperture. The insertion direction is oriented transversely to the axis and transversely to the fixing direction of the fixing element. In this way, it is possible to insert the rod element into the receiving opening not only along the axis, "axially" so to speak, but transversely thereto, laterally through the aperture. The surgeon can choose one of the insertion directions depending on the available space, application and/or surgical procedure, thus making the connection device more versatile and easier to handle.

A receiving space may be arranged at the respective connection region into which the rod element engages and in which receiving space the rod element is fixable by means of the fixing element.

It may be in particular advantageous that the rod element can be inserted into the receiving opening transversely to the fixing direction through the aperture. This preferably offers the possibility of pre-fixing the fixing element to the main body, inserting the rod element and then fixing it to the fixing element. This also favors improved handling of the connection device in accordance with the disclosure.

The term "transverse" may presently in particular mean and include "perpendicular".

The receiving opening in the first surface portion is also referred to hereinafter as the first receiving opening.

Advantageously, an opening width of the aperture is smaller than the opening width of the receiving opening in the first surface portion. This preferably reduces the probability of the rod element inserted into the receiving opening unintentionally coming out of the receiving opening again through the aperture, and improves the handling of the connection device.

Preferably, the receiving opening forms or comprises a recess with respect to the aperture, into which recess the rod element can be inserted and fixed therein by means of the fixing element. After passing through the aperture, the rod element can, for example, be inserted into the recess and fixed therein.

In a plan view along the axis, the main body may, for example, be substantially configured in a C-shape at least in sections, wherein the aperture is formed at the receiving opening edge between two legs of the C. The leg in the area of which the fixing element is arranged, can in particular be of longer extent than the other leg of the C.

For example, the leg of the C on the area of which the aforementioned recess is arranged is configured shorter than the other leg of the C. The short leg is, for example, the leg which is opposite the longer leg, in the area of which longer leg the fixing element is arranged.

It is favorable if a second receiving opening is formed in the second surface portion, with a receiving opening edge which has the aperture for inserting the rod element into the second receiving opening starting from the first surface portion and through the aperture, transversely to the axis. Arranged in the second receiving opening, the rod element in comparison to an arrangement in the first receiving opening has a different orientation with regard to different relative orientations with respect to the other rod element. The rod element can be inserted through the aperture not only into the first receiving opening, but, in a different orientation, into the second receiving opening. The direction of insertion in this regard is directed transversely to the axis of the second receiving opening and in particular transversely to the fixing direction.

It is advantageous if the receiving opening edge of the second receiving opening has a further aperture for inserting the rod element into the second receiving opening starting from a third surface portion of the main body facing away from the first surface portion and through the further aperture, transversely to the axis. This allows the rod element to be inserted into the second receiving opening in a different manner. The insertion direction in this regard is oriented transversely to the axis of the rod element and, in particular, opposite to the insertion direction into the second receiving opening starting from the first surface portion. In particular, the further insertion direction may be oriented transversely to the fixing direction. The further aperture increases the versatility of the connection device and thus improves its handling.

A third receiving opening is favorably formed in a third surface portion facing away from the first surface portion. The rod element can be inserted into the third receiving opening and fixed therein by means of the fixing element.

It is advantageous if a receiving opening edge of the third receiving opening has the aforementioned further aperture for inserting the rod element into the third receiving opening starting from the second surface portion and through the further aperture, transversely to the axis. This offers the possibility of inserting the rod element into the third receiving opening not only axially in the direction of extension of the rod element, but through the further aperture starting from the second surface portion. This increases the versatility of the connection device and improves its handling. In particular, the insertion direction in this regard is oriented transversely to the fixing direction.

In accordance with the above, it is preferably provided that the receiving opening edge of the second receiving opening has two apertures. A first aperture is formed in such a way that it is simultaneously an aperture of the receiving opening edge of the first receiving opening. A second aperture is formed in such a way that it is simultaneously an aperture of the receiving opening edge of the third receiving opening.

In particular, the main body can have edge portions with apertures formed there. A rod element can be inserted through one of the apertures into the first receiving opening or into the second receiving opening, depending on the selected insertion direction and orientation of the rod element. A rod element can be inserted through the second aperture into the second receiving opening or into the third receiving opening, depending on the selected insertion direction and orientation of the rod element.

It can be provided that the third receiving opening is oriented coaxially with the receiving opening in the first surface portion. This makes it possible, for example, to guide a rod element through the first and third receiving openings.

If the receiving opening edge of the first receiving opening and the receiving opening edge of the third receiving opening each have an aperture for inserting a rod element starting from the second surface portion, it is preferably possible in particular to insert a rod element into the first and third receiving openings through these two apertures starting from the second surface portion, transversely to the particular axis and in particular transversely to the fixing direction.

The third receiving opening preferably has a shape that is identical to the receiving opening in the first surface portion. The receiving openings may, in particular, be congruent.

It may be provided that an opening width of the aperture (for inserting the rod element into the second receiving opening starting from the first surface portion) is smaller than the opening width of the second receiving opening.

Alternatively or additionally, it can be provided that an opening width of the further aperture is smaller than the opening width of the second receiving opening.

Alternatively or additionally, it can be provided that an opening width of the further aperture is smaller than the opening width of the third receiving opening.

Due to the smaller opening width of a particular aperture in relation to a corresponding receiving opening, the probability of the rod element coming out of the receiving opening laterally is reduced. The handling of the connection device is thus improved.

In particular, it can be provided that the second receiving opening and/or the third receiving opening forms or comprises a recess with respect to the first-mentioned aperture or the further aperture, in which recess the rod element can be fixed by means of the fixing element. After passing through the aperture or the further aperture, the rod element can, for example, be inserted into the recess of the second receiving opening and fixed therein. In a corresponding manner, the rod element can, for example, be inserted into the third aperture and fixed therein after passing through the further aperture.

It may be provided that the second receiving opening has a shape that differs from the shape of the receiving opening in the first surface portion (first receiving opening) and/or from the shape of the third receiving opening.

It is favorably provided that the second receiving opening defines an axis that is oriented perpendicularly to the axis of the receiving opening in the first surface portion (first receiving opening) and/or to the axis of the third receiving opening. In particular, the axes may intersect.

In a preferred embodiment, it is provided that the second surface portion is oriented perpendicularly to the first surface portion and/or perpendicularly to the third surface portion.

Alternatively or additionally, it may be provided that the first and third surface portion are parallel to one another.

The fixing element allows, for example, force-locking or positive-locking fixing of the rod element and is configured to be fixed to the connection region for example in a force-locking and/or positive-locking manner.

A fixing element receptacle is, for example, formed on the respective connection region for the respective fixing element. Provision may preferably be made, in particular, for an edge of at least one fixing element receptacle to be of closed-loop configuration and/or free of an aperture. In this way, a reliable fit of the fixing element in the fixing element receptacle can be ensured.

In particular, provision is preferably not made for a rod element to be insertable through an aperture of an edge of the fixing element receptacle into one of the receiving openings.

In a preferred embodiment, the fixing element is, for example, a screw element which can be screwed in the fixing direction into a screw receptacle on the main body, the rod element being fixable in a clamped manner at the connection region by means of the screw element. The screw receptacle forms the aforementioned fixing element receptacle and has in particular a thread which can be brought into engagement with the thread of the screw element.

In particular, it can be provided that a receiving opening with a receiving opening edge having an aperture is provided only in one connection region, as mentioned above.

It is favorable if two receiving openings formed on surface portions facing away from one another are formed in the first connection region and in the second connection region, the rod elements being insertable into the receiving openings in opposite directions. This gives the possibility of connecting the rod elements axially to one another by means of the connection device, with one of the rod elements being fixed to each of the two connection regions. The receiving openings may be oriented coaxially to one another and define axes that are in alignment with one another. For rod elements of the same diameter, axes of the rod elements can be aligned with one another. For rod elements of different diameters, the axes of the rod elements can be parallel to one another.

Preferably, the main body comprises a stop element for at least one of the rod elements, which stop element is effective in one of the insertion directions. The stop element on the main body may serve in particular to ensure that at least one of the rod elements assumes a defined relative position to the main body. This improves the manageability of the connection device.

The stop element delimits for example the aforementioned receiving spaces of the connection regions.

In a preferred embodiment, the stop element can be configured as a partition wall of the main body. In particular, one stop element, especially the partition wall, can be effective for both of the rod elements. The partition wall may be entirely closed and be free of an opening.

The connection regions are connected rigidly to one another in a preferred embodiment. This may in particular be understood to mean that the connection regions are connected to each other so firmly that they are not fixable to one another in a movable manner. In fact, a non-movable connection of the connection regions can be provided in the preferred embodiment.

Advantageously, at least one receiving opening is formed in the first connection region and at least one further receiving opening is formed in the second connection region, which receiving openings define axes which are oriented transversely and in particular perpendicularly to one another. This makes it possible to connect the rod elements at an angle relative to one another by means of the connection device. In particular, a right-angled connection can be provided here, with the rod elements being oriented in an L-shape relative to one another, for example.

Preferably, at least one receiving opening is formed in the first connection region and at least one further receiving opening is formed in the second connection region, which receiving openings define axes which are parallel to one another. This makes it possible to connect two rod elements oriented parallel to one another by means of the connection device.

In the two last-mentioned advantageous embodiments, it is favorable if two receiving openings oriented coaxially with one another are formed in at least one of the connection regions, and if the rod element is configured to be guided through the two receiving openings. For example, these receiving openings are formed on two sides of the corresponding connection region facing away from one another, and the rod element is configured to be guided through the receiving openings and the main body. The receiving openings can be in particular of identical form and/or congruent.

It is favorable if at least one of the connection regions is configured for fixing rod elements of different diameters. This can be facilitated, for example, by the shape of the receiving openings as explained in the following.

In a preferred embodiment of the connection device, at least one receiving opening with a circular or with an non-round cross section is provided.

It is favorable if there is provided at least one receiving opening of which the receiving opening edge runs in segments along a circular arc with a first radius and in segments along a circular arc with a second radius, which is different from the first radius and in particular is smaller than the first radius. The different radii make the receiving opening better suited to fixing rod elements of different radii. For example, a rod element with a smaller radius can be placed against the circular arc with the second radius (if this is the smaller radius). A rod element with a larger radius can be placed against the circular arc with the first radius (if this is the larger radius).

It may prove favorable if there is provided at least one receiving opening of which the receiving opening edge has two planar segments oriented in a V shape relative to one another. The segments make it possible to adapt a plurality of rod elements of different radii equally to the receiving opening edge.

The receiving opening edge, between the planar segments, which are oriented in a V-shape to one another, preferably has a segment with a radius.

The object mentioned at the outset is achieved by a surgical connection system in accordance with the disclosure, which comprises at least one connection device of the above-mentioned type and two or more rod elements, which are fixable selectively at the first connection region and/or at the second connection region.

The advantages already mentioned in conjunction with the explanation of the connection device in accordance with the disclosure can also be achieved with the connection system. To avoid repetition, reference can be made to the above explanations.

Advantageous embodiments of the connection system in accordance with the disclosure result from advantageous embodiments of the connection device in accordance with the disclosure. In this respect too, reference is made to the above explanations.

The rod elements can be configured to be identical. Alternatively or additionally, at least two differently configured rod elements can be provided. For example, at least two rod elements with different radii are provided.

Figure 5:
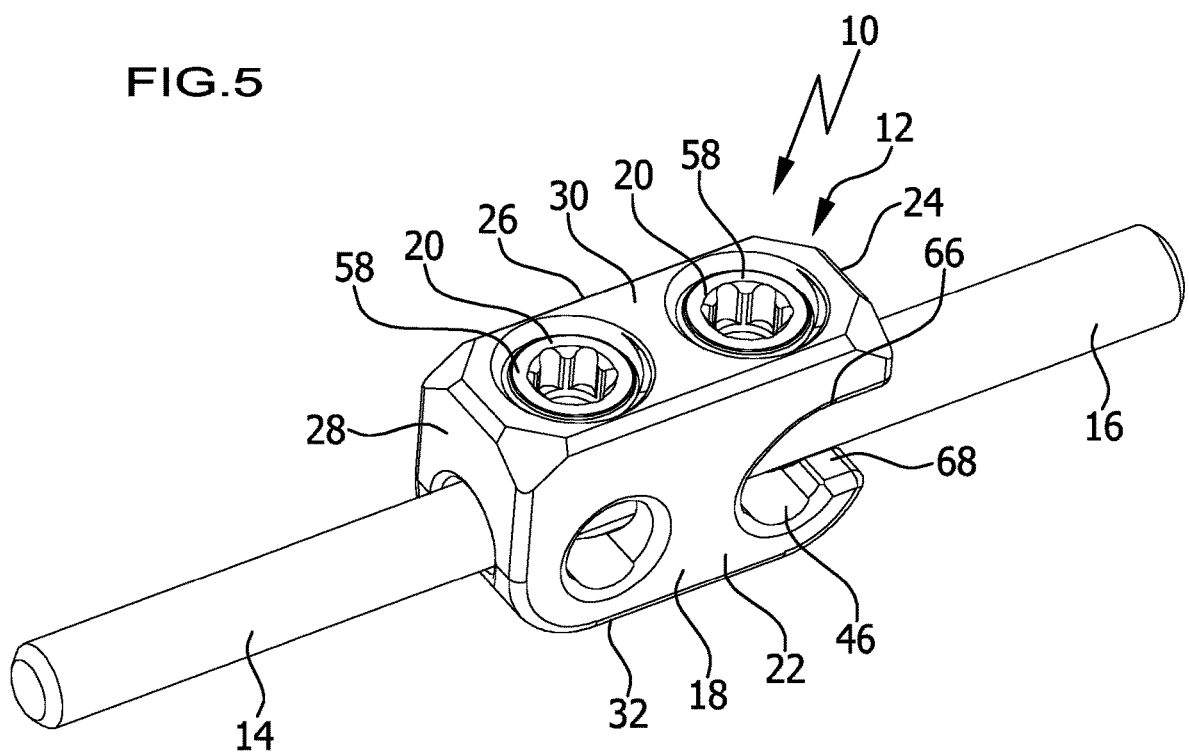
FIG. 5: shows a second perspective view of the connection system from FIG. 1, wherein the rod elements assume a second relative orientation.
Figure 6:
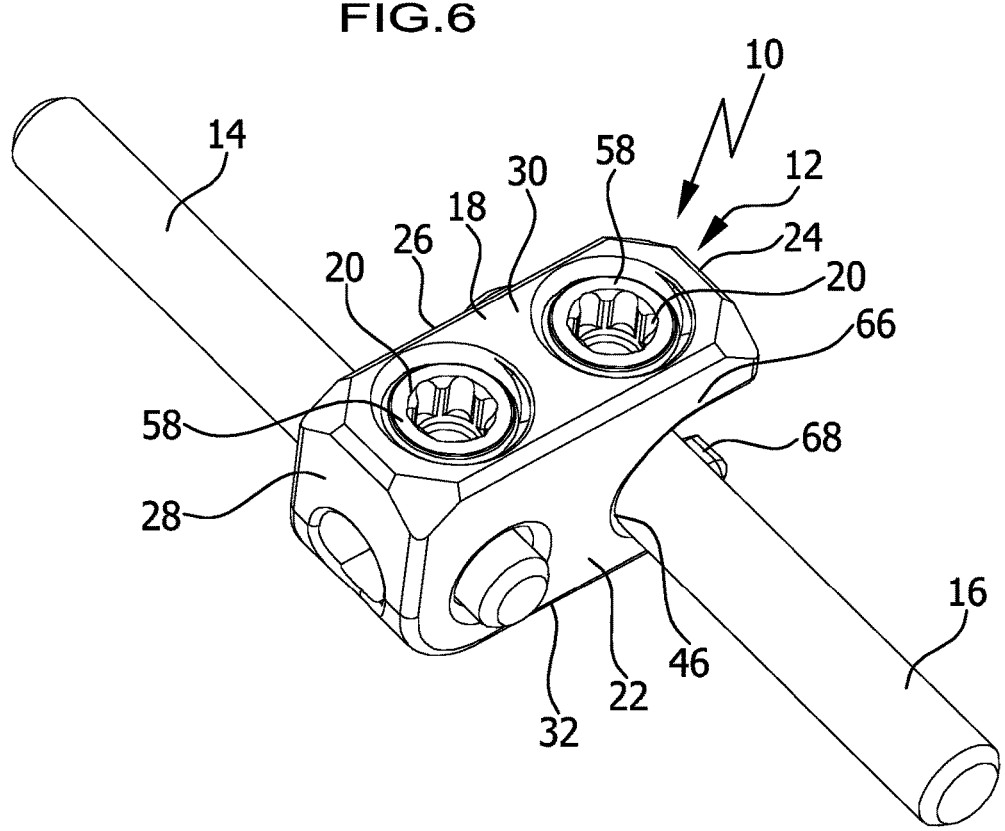
FIG. 6: shows a third perspective view of the connection system from FIG. 1, wherein the rod elements assume a third relative orientation.

FIGS. 1, 5 and 6 each show a perspective view of a preferred embodiment of a connection system 10 in accordance with the disclosure. The connection system 10 comprises a preferred embodiment of a versatile and universally applicable connection device 12 in accordance with the disclosure and at least two rod elements 14, 16.

As will become clear from the following explanations and as can be seen directly from FIGS. 1, 5 and 6, the rod elements 14, 16 can preferably be connected in different relative orientations to one another by means of the connection device 12. The different relative arrangements include in particular an L-shaped relative orientation (FIG. 1), an axial connection (FIG. 5) and a relative orientation in parallel of the rod elements 14, 16 (FIG. 6).

The connection device 12 comprises a main body 18 and two fixing elements 20. The main body 18 is formed in one piece in the present case.

In the present case, the basic shape of the main body 18 is approximately cuboidal or is based on a cuboidal shape. The main body 18 has a first surface portion 22 and, adjacently thereto, a second surface portion 24, which is oriented transversely and, in particular, perpendicularly to the first surface portion 22.

The main body 18 has a third surface portion 26, which is adjacent to the second surface portion 24 and is oriented transversely and, in particular, perpendicularly thereto. The surface portions 22 and 26 are arranged on sides of the main body 18 facing away from one another.

A fourth surface portion 28 connects the surface portions 22, 26 to one another and is oriented transversely and, in particular, perpendicularly thereto. The surface portions 24, 28 are arranged on sides of the main body 18 facing away from one another.

Furthermore, a fifth surface portion 30 and a sixth surface portion 32 are provided, on sides of the main body 18 facing away from one another. The surface portions 30, 32 are in each case adjacent to the other surface portions 22 to 28.

It is understood that bevels or chamfers may be present on the main body 18 in the region of the transitions of mutually adjacent surface portions 22 to 32 and/or on corner regions of the main body 18.

The main body 18 is generally mirror-symmetrical with respect to a median longitudinal plane 34. The median longitudinal plane 34 is located centrally between the surface portions 22 and 26 and runs parallel to the planes defined by these two surface portions.

The main body 18 comprises a first connection region 36 and a second connection region 38. One of the rod elements 14, 16 can be fixed at the first connection region 36. The drawing shows this using the example of the rod element 14. The other rod element 14, 16 can be fixed at the second connection region 38. This is shown in the drawing using the example of the rod element 16.

The connection regions 36, 38 are separated from one another, for example, by a transverse plane 40 of the main body 18. The transverse plane 40 is directed perpendicularly to the median longitudinal plane 34 and is arranged approximately centrally between the surface portions 24 and 28.

Figure 7:
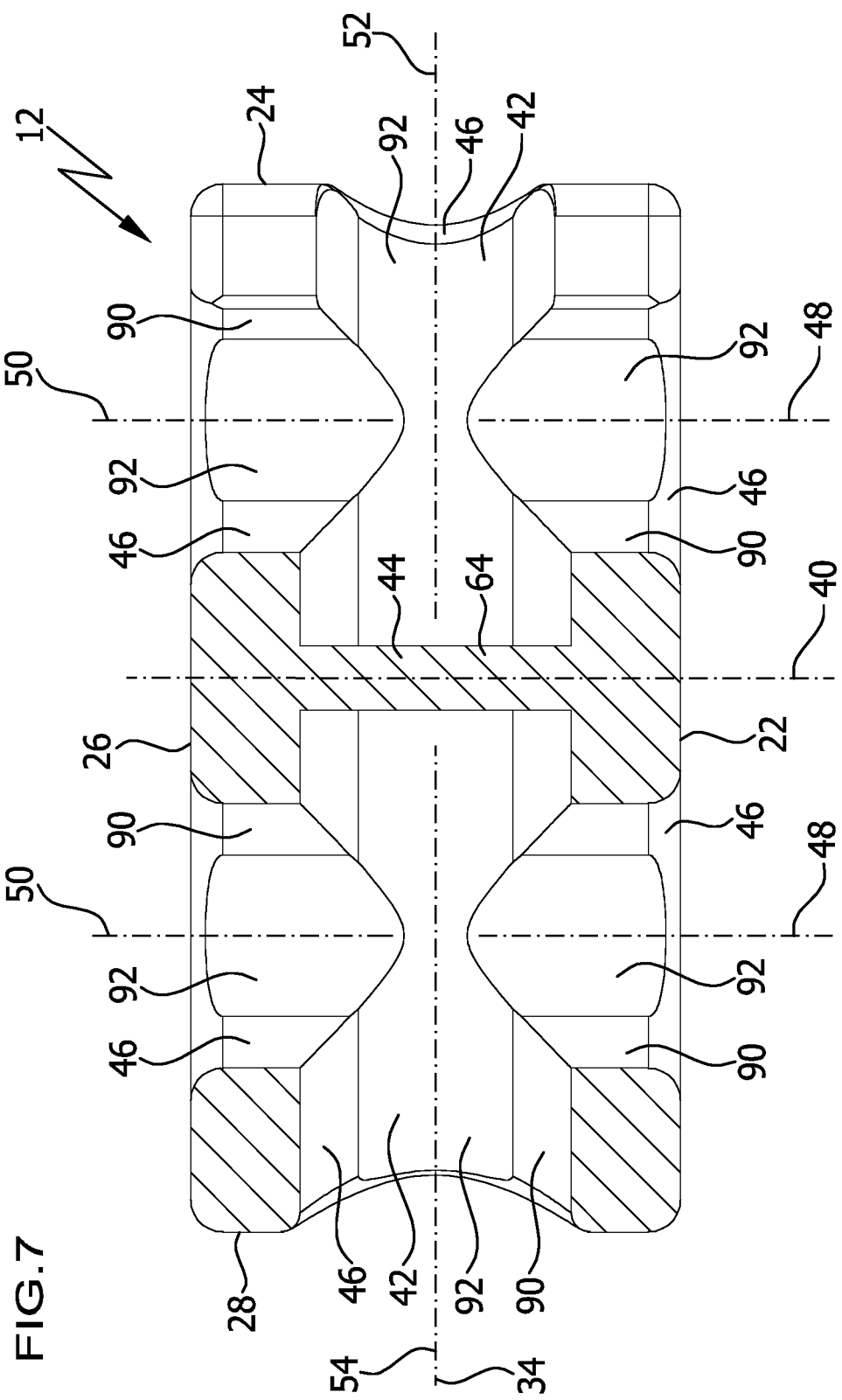
FIG. 7: shows a sectional view along line 7-7 in FIG. 3.

As can be seen in particular from FIG. 7, a cavity 42 is formed in the main body 18 in each connection region 36, 38. The cavities 42 are separated from one another by a partition wall 44, through which the transverse plane 40 runs.

The cavity 42 is presently a receiving space formed at the respective connection region 36, 38. A respective rod element 14, 16 can engage in the cavity 42. The cavity 42 is a receiving space of the connection region 36 or 38.

To insert the rod elements 14, 16 into the respective cavity 42, a plurality of receiving openings are formed on the main body 18 in the surface portions 22 to 28. The receiving openings are each designated by the reference numeral 46. A rod element 14, 16 can be inserted into or guided through one of the connection regions 36, 38 while engaging in the cavity 42 via a receiving opening 46. In this way, the different relative orientations of the rod elements 14, 16 shown in FIGS. 1, 5 and 6 can be realized, depending on the orientation of the rod elements 14, 16 in the receiving openings 46.

Each receiving opening 46 has an axis. The axis can in particular be regarded as the direction in which a rod element 14, 16 in a receiving opening 46 projects out from the main body 18. This is, for example, an axis of the respective receiving opening 46.

The receiving openings 46 in the first surface portion 22 have an axis 48. The receiving openings 46 in the third surface portion 26 have an axis 50 that is opposite to the axis 48.

The receiving opening 46 in the second surface portion 24 has an axis 52 which is directed transversely and in particular perpendicularly to the axes 48, 50.

The receiving opening 46 in the fourth surface portion 28 has an axis 54 which is directed oppositely to the axis 52 and is directed transversely and in particular perpendicularly to the axes 48, 50.

In order to fix the rod elements 14, 16 at the connection regions 36 and 38, respectively, the connection device 12 comprises the fixing elements 20. In the present case, two fixing elements 20 are provided, each of which is formed as a screw element 58 and is arranged in a screw receptacle 60 in the connection regions 36, 38. The screw receptacles 60 are formed in the fifth surface portion 30.

The screw receptacle 60 is a fixing element receptacle for the fixing element 20. An edge of the respective screw receptacle 60 is of closed-loop configuration and free of an aperture. In particular, none of the rod elements 14, 16 can be inserted into one of the receiving openings 46 through such an aperture of the edge of the screw receptacle 60.

The screw elements 58 can be screwed in in a fixing direction 62, which is directed towards the cavity 42 and the sixth surface portion 32. Depending on how thick the rod element 14, 16 is, the screw elements 58 engage into the cavity 42 to a greater or lesser extent. The rod elements 14, 16 are fixed to the main body 18 in a clamping manner by means of the screw elements 58.

Figure 3:
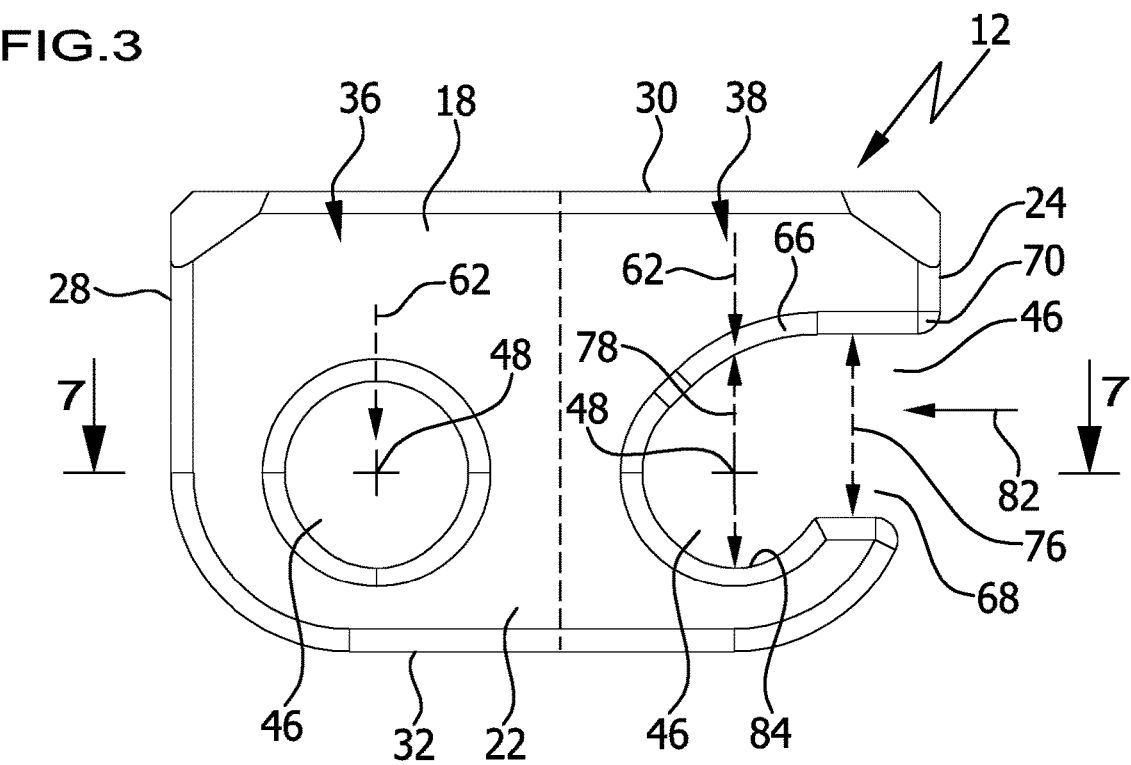

The first connection region 36 comprises a receiving opening 46 in each of the surface portions 22, 26 and 28. The receiving openings 46 in the surface portions 22 and 26 are oriented coaxially with one another (FIG. 3). Furthermore, the receiving openings 46 in the surface portions 22 and 26 are of identical shape and congruent to one another.

The axes 48 and 50 are aligned with one another, but with regard to their orientation are directed oppositely from one another away from the main body 18. The axis 54 is directed transversely and in particular perpendicularly to the axes 48, 50.

In the first connection region 36, the rod element 14 may be arranged as follows:

Firstly, it is possible to orient the rod element 14 along the axis 54 and through the receiving opening 46 in the fourth surface portion 28 (FIGS. 1 and 5). Preferably, the partition wall 44 serves as a stop element 46 for the rod element 14.

Secondly, it is possible to orient the rod element 14 along the axis 48 or 50 only through the receiving opening 46 in the first surface portion 22 or only through the receiving opening 46 in the third surface portion 26. This is not shown in the drawing.

Thirdly, it is possible to guide the rod element 14 through the main body 18 through both receiving openings 46 of the surface portions 22, 26. This is shown in FIG. 6, in which case the rod element 16 protrudes from the main body 18 along the axis 50.

Also, in the second connection region 38, as mentioned, receiving openings 46 are provided for engaging the rod element 16 into the cavity 42 or for passing it through the main body 18.

Figure 2:
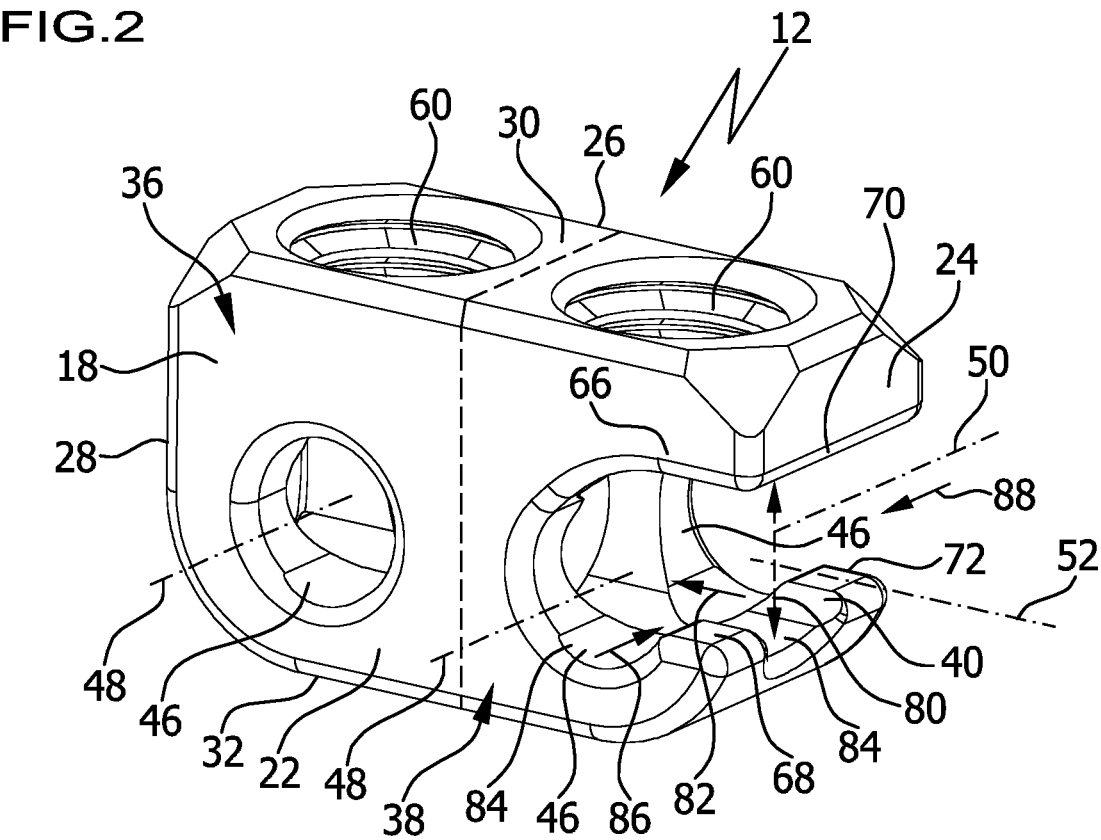
FIG. 2: shows a perspective view of a main body of the connection device from FIG. 1, FIG. 3: shows a side view of the main body.

As can be seen in particular from FIGS. 2 and 3, a receiving opening 46 is formed in the first surface portion 22 and has a receiving opening edge 66. The receiving opening edge 66 has an aperture 68 in the direction of the second surface portion 24.

A receiving opening 46 is formed in the second surface portion 22 and has a receiving opening edge 70. The receiving opening edge 70 has two apertures. These include the aforementioned aperture 68 in the direction of the first surface portion 22. In addition, a further aperture 72 is provided opposite the aperture 68 and extends as far as the third surface portion 26.

Figure 4:
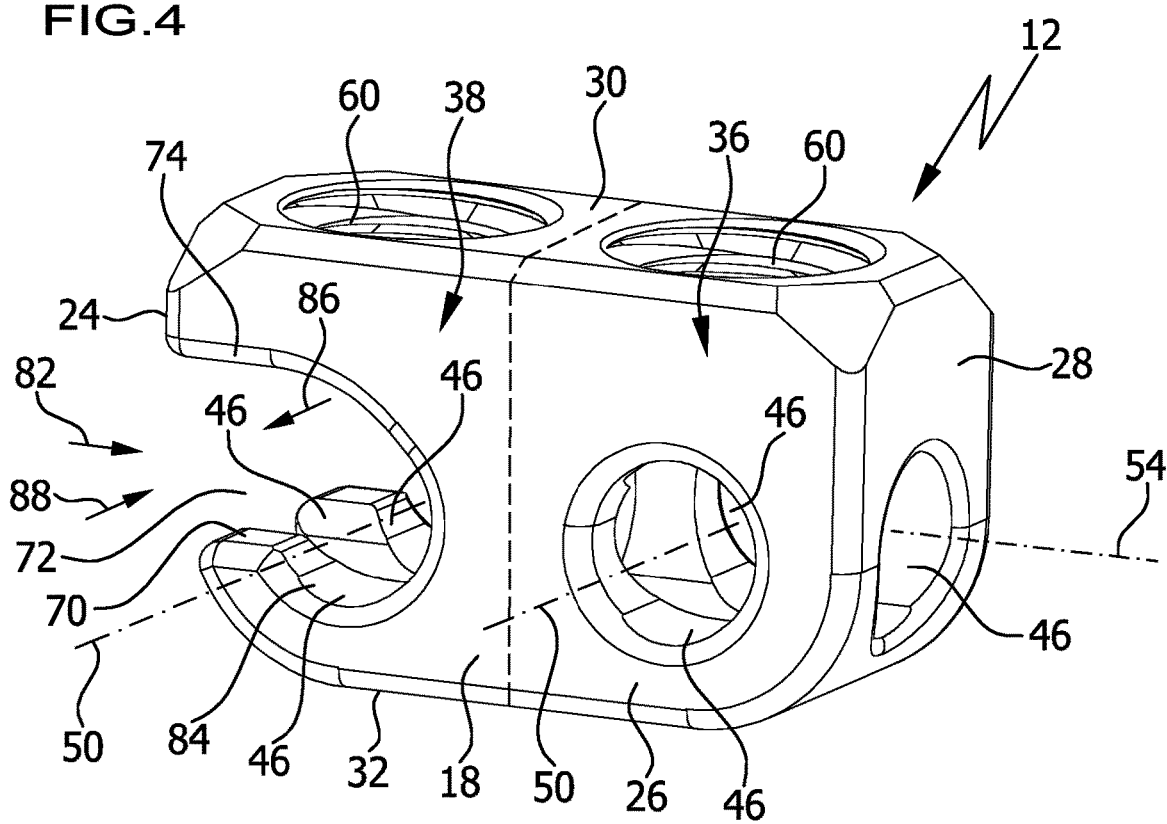
FIG. 4: shows another perspective view of the main body.

As shown in particular in FIG. 4, a receiving opening 46 is formed in the third surface portion 26 and has a receiving opening edge 74. The receiving opening edge 74 has an aperture. This is the aperture 72, which extends as far as the second surface portion 24.

The receiving openings 46 in the surface portions 22 and 26 are in the present case identical in shape and oriented coaxially with one another as well as congruent to one another.

The configuration explained above can be expressed, in the present example of the main body 18, to the effect that the main body 18 has two apertures in the second connection region 38. The first aperture 68 is an aperture of the receiving opening edges 66 and 70 and is formed in the transition between the surface portions 22 and 24. The further aperture 72 is an aperture of the receiving opening edges 70 and 74 and is formed in the transition of the surface portions 24 and 26.

As can be seen in particular from FIGS. 2 to 4, the apertures 68, 72 are provided in the present case with an identical opening width 76. In a preferred embodiment, the opening width 76 can be smaller than the opening width 78 of the receiving openings 46 in the surface portions 22 and 26 and smaller than an opening width 80 of the receiving opening 46 in the surface portion 24.

In the connection device 12, the following advantages exist as a result of the apertures 68, 72:

Starting from the second surface portion 24, the rod element 16 can be inserted through the aperture 68 into the receiving opening 46 in the first surface portion 22. An arrow 82 indicates the insertion direction in this regard. The insertion direction 82 is directed transversely to the axis 48 and transversely to the fixing direction 62.

This makes it possible to insert the rod element 16 into the receiving opening 46 not only along the axis 48, but also via the lateral aperture 68. This increases the versatility of the connection device 12 and improves its handling. In particular, it is possible to insert the rod element 16 into the receiving opening 46 with the screw element 58 already preassembled.

Advantageously, the receiving opening 46 in the surface portion 22 has a recess 84 with respect to the aperture 68. This reduces the probability that the rod element 16, once inserted into the receiving opening 46, will unintentionally come out again through the aperture 68.

The rod element 16 can, for example, be inserted through the aperture 68 into the recess 84 and be secured in it by means of the screw elements 58.

As can be seen, in particular, in FIG. 3, the main body 18 substantially has at the connection region 38 substantially a C-shape in a plan view along the axis 48. In the area of a first leg, shown in the drawing on top, the fixing element 20 is arranged (with respect to the drawing plane behind the leg). The recess 84 is arranged on a second leg which is opposite the first leg and shown on the bottom in the drawing.

The second leg is presently shorter than the first leg so that the free end of the second leg is set back in relation to the free end of the first leg on which the surface portion 24 is arranged on the front end, in the present case in the direction of the connection region 36.

The advantages explained using the example of the receiving opening 46 in the surface portion 22 apply correspondingly to the receiving openings 46 in the third surface portion 26 and in the second surface portion 24.

In particular, the above explanations for the receiving opening 46 in the third surface portion 26 can be directly assigned due to the symmetrical configuration of the main body 18. It is possible to insert the rod element 16 into the receiving opening 46 through the further aperture 72 in the insertion direction 82, starting from the second surface portion 24.

As explained above using the example of the first connection region 36, for fixing the rod element 16 at the second connection region 38, it can be provided that the rod element projects into the cavity 42 through only one of the receiving openings 46 in the surface portions 22 or 26 and is fixed therein by means of the screw element 58.

Furthermore, it is possible for the rod element 16 to project through both receiving openings 46 in the surface portions 22 and 26 (FIGS. 1 and 6). For this purpose, the provision of the apertures 68, 72 offers the possibility of inserting the rod element 16, starting from the second surface portion 24, into these two receiving openings 46 in the insertion direction 82.

At the receiving opening 46 in the second surface portion 24, it is possible to insert the rod element 16 along the axis 52. In particular, the partition wall 44 can be effective as a stop element 64.

Through the aperture 68, the rod element 16 can alternatively be inserted into the receiving opening 46 in the second surface portion 24, starting from the first surface portion 22, transversely to the axis 52 and transversely to the fixing direction 62. An arrow 86 indicates the insertion direction in this regard Correspondingly, the rod element 16 can alternatively be inserted into the receiving opening 46 in the second surface portion 24 starting from the third surface portion 26 in an insertion direction indicated by an arrow 88, transversely to the axis 52 and transversely to the fixing direction 62.

In both cases, the rod element 16 can be inserted into the recess 84 of the receiving opening 46 on the second surface portion 24 after insertion through the aperture 68 or 72 and be fixed in the recess 84 by means of the screw element 58.

In the latter two cases, there is the possibility of an axial displacement of the rod element 16 until it strikes against the stop element 64.

The connection system 10 has the advantage that the screw element 58 can be pre-fixed in the screw receptacle 60 on the connection region 38 before the rod element 16 is inserted. The rod element can be inserted through one of the receiving openings 46 on the first, second or third surface portions 22, 24, 26 and be secured by means of the already pre-fixed screw element 58 on the connection region 38.

The receiving openings 46 of the surface portions 24 and 28 are oriented coaxially with one another to allow an axial connection of the rod elements 14, 16 (FIG. 5). Depending on the diameters of the rod elements 14, 16, their axes, for example, are aligned with one another (in the case of matching diameters), or their axes are parallel to one another (in the case of different diameters). In the latter case, the rod elements 14, 16 are parallel to one another.

A relative orientation in parallel of the rod elements 14, 16 is possible by inserting them into the receiving openings 46 of the first and third surface portion 22, 26 (FIG. 6).

On the one hand, an L-shaped relative orientation of the rod elements 14, 16 may be achieved by inserting the rod element 14 into the receiving opening 46 in the fourth surface portion 28 and the rod element 16 into at least one of the receiving openings 46 in the first and third surface portion 22, 26. On the other hand, the rod element 16 may be inserted into the receiving opening 46 in the second surface portion 24 and the rod element 14 into at least one receiving opening 46 in the first and in the third surface portion 22, 26.

As mentioned above, it is favorable if rod elements 14, 16 of different diameter are insertable into a respective receiving opening 46.

Figure 8:
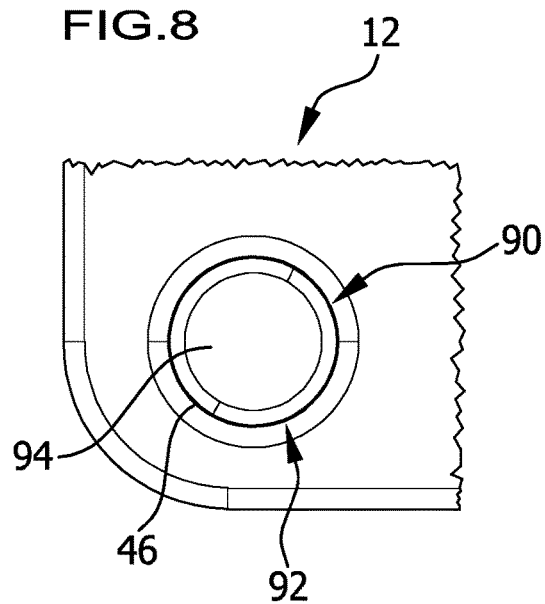
FIG. 8: shows an enlarged view of a portion of the connection system, showing a receiving opening with a first rod element arranged therein.
Figure 9:
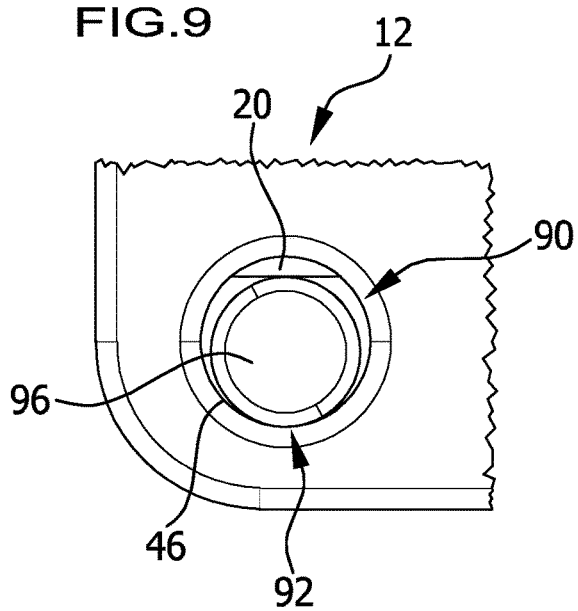
FIG. 9: shows an enlarged view of a portion of the connection system, showing a receiving opening with a second rod element arranged therein.

FIGS. 8 and 9 show a detailed view of the receiving opening 46 of the connection region 36 in the surface portion 22. It can be seen that the receiving opening 46 is not an opening with a circular cross section. Instead, two segments 90, 92 are provided, each running along an arc of a circle. However, the segments 90, 92 differ in their radii. The radius of the segment 92 is smaller than the radius of segment 90.

The other receiving openings 46 in the main body 18 also have segments with different radii. However, the receiving openings 46 in the second connection region 38 comprise segments 90 of different length as a result of the presence of the apertures 68, 72.

The provision of segments 90, 92 of different radii offers the advantage that rod elements of different diameter can be reliably fixed in the receiving opening 46. FIG. 8 illustrates this for a rod element 94 with a larger radius, which is adapted to the radius of segment 90. FIG. 9 shows this for a rod element 96 with a smaller radius, which is adapted to the radius of the segment 92. In each case, there is the possibility of areal contact at the edge of the receiving opening 46.

Figure 10:
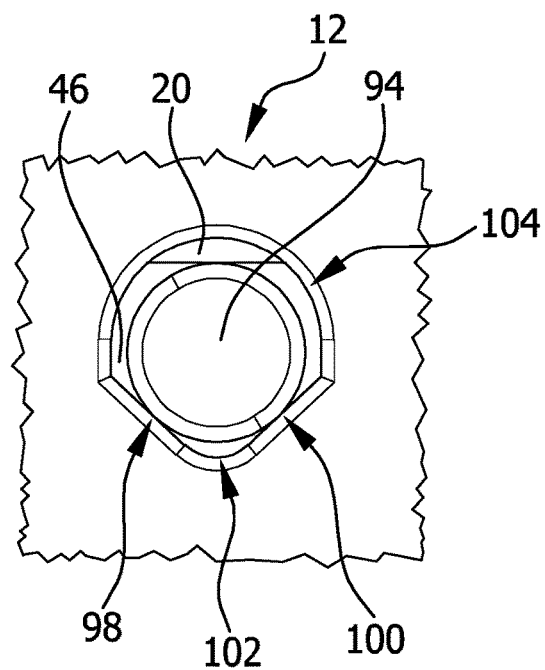
FIG. 10: shows a view similar to FIGS. 8 and 9 in a further preferred embodiment, wherein a first rod element is arranged in a receiving opening.
Figure 11:
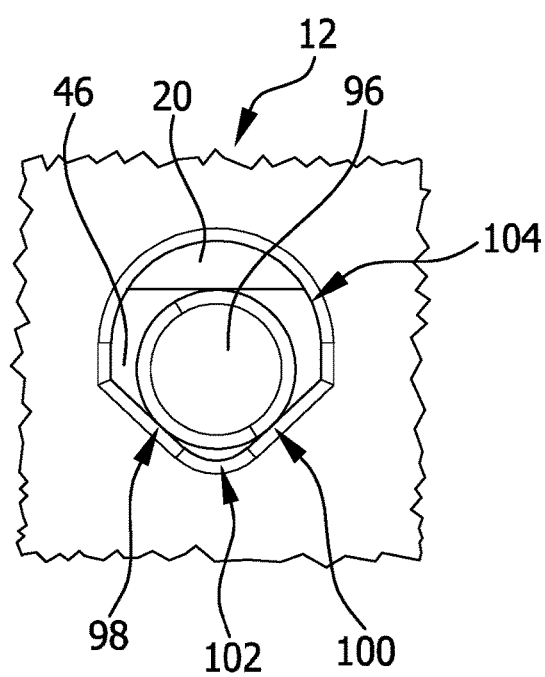
FIG. 11: shows a view similar to FIGS. 8 and 9 in a further preferred embodiment, wherein a second rod element is arranged in a receiving opening.

FIGS. 10 and 11 show a different shape of a receiving opening 46 in the main body 18. Here, the receiving opening 46 has two planar segments 98, 100 which are oriented in a V-shape relative to one another. The angle between the segments 98, 100 is approximately 90°.

A segment 102 with a radius and approximately in a circular arc shape is provided between the segments 98, 100. Another segment 104 connects the segments 98, 100 at their ends directed away from one another and is semi-circular in shape with a radius and with portions that extend in a straight line and adjoin the segments 98, 100, facing towards them.

Based on the rod elements 94 with a larger radius and the rod elements 96 with a smaller radius shown in FIGS. 10 and 11, it can be seen that such a configuration also allows for the possibility of reliably clamping rod elements of different diameter.

The invention claimed is:

1. A surgical connection device for connecting a first rod element to a second rod element in one or more relative orientations, wherein the connection device comprises a main body with a first connection region for the first rod element and a second connection region for the second rod element, wherein at least three receiving openings are formed in the main body, wherein at least one of the receiving openings is arranged in each connection region and at least one connection region has two or more of the receiving openings with different axes from one another, into which receiving openings the respective rod element is insertable selectively, and wherein in each connection region there is arranged a fixing element for fixing the respective rod element at the connection region in a fixing direction, wherein one of the receiving openings is formed in a first surface portion of the main body, said one of the receiving openings having a receiving opening edge having an aperture that extends from the first surface portion to an adjacent second surface portion of the main body being angled with respect to the first surface portion, for inserting the respective rod element into the receiving opening starting from the second surface portion and through the aperture, in an insertion direction transverse to the axis and transverse to the fixing direction,
wherein the receiving opening in the first surface portion forms or comprises a first recess with respect to the aperture,
wherein the respective rod element is insertable into the first recess and is fixable in the first recess by the fixing element,
wherein a second receiving opening is formed in the second surface portion, the second receiving opening comprising a receiving opening edge which has the aperture for inserting the respective rod element into the second receiving opening starting from the first surface portion and through the aperture, transversely to the axis of the second receiving opening,
wherein the second receiving opening forms or comprises a second recess with respect to the aperture, and
wherein the respective rod element is insertable into the second recess and is fixable in the second recess by the fixing element.

2. The surgical connection device according to claim 1, wherein the fixing element is pre-fixable to the main body whereupon the respective rod element is insertable through the aperture and then fixable by the fixing element.

3. The surgical connection device according to claim 1, wherein an opening width of the aperture is smaller than an opening width of the receiving opening in the first surface portion.

4. The surgical connection device according to claim 1, wherein an opening width of the aperture is smaller than the opening width of the second receiving opening.

5. The surgical connection device according to claim 1, wherein the receiving opening edge of the second receiving opening has a further aperture for inserting the respective rod element into the second receiving opening starting from a third surface portion of the main body facing away from the first surface portion and through the further aperture, transversely to the axis of the second receiving opening.

6. The surgical connection device according to claim 1, wherein a third receiving opening is formed in a third surface portion facing away from the first surface portion.

7. The surgical connection device according to claim 6, wherein a receiving opening edge of the third receiving opening has a further aperture for inserting the respective rod element into the third receiving opening starting from the second surface portion and through a further aperture, transversely to the axis of the third receiving opening.

8. The surgical connection device according to claim 7, wherein at least one of:
an opening width of the further aperture is smaller than an opening width of the third receiving opening, and
the third receiving opening forms or comprises a third recess with respect to the further aperture into which the respective rod element is fixable by the fixing element.

9. The surgical connection device according to claim 1, wherein a fixing element receptacle is formed for a fixing element on the main body wherein an edge of the fixing element receptacle is at least one of closed-loop configuration and free of an aperture.

10. The surgical connection device according to claim 1, wherein the first and second connection regions are rigidly connected to one another.

11. The surgical connection device according to claim 1, wherein two receiving openings formed on surface portions facing away from one another are formed in the first connection region and in the second connection region, and wherein the first and second rod elements are insertable into the receiving openings in mutually opposite directions, wherein the main body comprises a stop element for at least one of the rod elements which stop element is effective in one of the insertion directions.

12. The surgical connection device according to claim 1, wherein at least one receiving opening is formed in the first connection region and at least one further receiving opening is formed in the second connection region, which receiving openings define axes which are oriented transversely to one another.

13. The surgical connection device according to claim 1, wherein at least one receiving opening is formed in the first connection region and at least one further receiving opening is formed in the second connection region, which receiving openings define axes which are parallel to one another.

14. The surgical connection device according to claim 1, wherein two receiving openings oriented coaxially with one another are formed in at least one of the connection regions, and wherein the respective rod element is guidable through the two receiving openings.

15. The surgical connection device according to claim 1, wherein at least one receiving opening is provided with a circular or with a non-round cross section.

16. The surgical connection device according to claim 1, wherein there is provided at least one receiving opening of which the receiving opening edge runs in segments along a circular arc with a first radius and in segments along a circular arc with a second radius, which is different from the first radius.

17. The surgical connection device according to claim 1, wherein there is provided at least one receiving opening of which the receiving opening edge has two planar segments oriented in a V shape relative to one another.

18. A surgical connection device for connecting a first rod element to a second rod element in one or more relative orientations, wherein the connection device comprises a main body with a first connection region for the first rod element and a second connection region for the second rod element, wherein at least three receiving openings are formed in the main body, wherein at least one of the receiving openings is arranged in each connection region and at least one connection region has two or more of the receiving openings with different axes from one another, into which receiving openings the respective rod element is insertable selectively, and wherein in each connection region there is arranged a fixing element for fixing the respective rod element at the connection region in a fixing direction, wherein one of the receiving openings is formed in a first surface portion of the main body, the receiving opening edge of which receiving opening has an aperture which extends from the first surface portion to an adjacent second surface portion of the main body being angled with respect to the first surface portion, for inserting the respective rod element into the receiving opening starting from the second surface portion and through the aperture, in an insertion direction transverse to the axis and transverse to the fixing direction,
- wherein two receiving openings formed in surface portions facing away from one another are formed in the first connection region and in the second connection region, wherein the first and second rod elements are insertable into the receiving openings in mutually opposite directions, and wherein the main body comprises a stop element for at least one of the first and second rod elements which stop element is effective in both of the insertion directions, which stop element is configured as an entirely closed partition wall of the main body.

19. A surgical connection system, comprising at least one connection device and two or more rod elements, the connection device being adapted for connecting a first rod element to a second rod element in one or more relative orientations, wherein the connection device comprises a main body with a first connection region for the first rod element and a second connection region for the second rod element, wherein at least three receiving openings are formed in the main body, wherein at least one of the receiving openings is arranged in each connection region and at least one connection region has two or more of the receiving openings with different axes from one another, into which receiving openings the respective rod element is insertable selectively, and wherein in each connection region there is arranged a fixing element for fixing the respective rod element at the connection region in a fixing direction, wherein one of the receiving openings is formed in a first surface portion of the main body, the receiving opening edge of which receiving opening has an aperture which extends from the first surface portion to an adjacent second surface portion of the main body being angled with respect to the first surface portion, for inserting the respective rod element into the receiving opening starting from the second surface portion and through the aperture, in an insertion direction transverse to the axis and transverse to the fixing direction, and wherein the rod elements are fixable selectively to at least one of the first connection region and the second connection region,
- wherein the receiving opening in the first surface portion forms or comprises a first recess with respect to the aperture,
- wherein the respective rod element is insertable into the first recess and is fixable in the first recess by the fixing element,
- wherein a second receiving opening is formed in the second surface portion, the second receiving opening comprising a receiving opening edge which has the aperture for inserting the respective rod element into the second receiving opening starting from the first surface portion and through the aperture, transversely to the axis of the second receiving opening,
- wherein the second receiving opening forms or comprises a second recess with respect to the aperture, and
- wherein the respective rod element is insertable into the second recess and is fixable in the second recess by the fixing element.

* * * * *